United States Patent [19]

Draghetti

[11] Patent Number: 5,695,070
[45] Date of Patent: Dec. 9, 1997

[54] UNIT FOR SAMPLING AND QUALITY CONTROLLING TOBACCO ITEMS, PARTICULARLY CIGARETTES

[75] Inventor: Fiorenzo Draghetti, Medicina, Italy

[73] Assignee: G.D Societa' Per Azioni, Bologna, Italy

[21] Appl. No.: 438,388

[22] Filed: May 10, 1995

[30] Foreign Application Priority Data

May 11, 1994 [IT] Italy ................... BO94A0207

[51] Int. Cl.⁶ .................. B07C 5/00; B65G 53/08; A24C 1/14
[52] U.S. Cl. .................. 209/536; 209/538; 209/906; 209/919; 209/932; 198/471.1; 406/34; 406/68; 131/282; 131/908
[58] Field of Search .................. 209/535, 536, 209/538, 539, 576, 577, 906, 919, 932, 644; 198/380, 438, 471.1, 493; 406/34, 68, 74; 131/281, 282, 904, 907, 908

[56] References Cited

U.S. PATENT DOCUMENTS

| | | |
|---|---|---|
| 4,158,625 | 6/1979 | Takahashi et al. ............... 209/538 X |
| 4,399,757 | 8/1983 | Maury ............................. 406/68 X |
| 5,232,079 | 8/1993 | Belcastro ........................ 198/372 |
| 5,366,096 | 11/1994 | Miller ........................... 209/538 X |

FOREIGN PATENT DOCUMENTS

| | | |
|---|---|---|
| 0110125 | 10/1983 | European Pat. Off. . |
| 53-96866 | 8/1978 | Japan .......................... 209/535 |
| 1028372 | 5/1966 | United Kingdom . |
| 2120075 | 11/1983 | United Kingdom . |
| 2178293 | 2/1987 | United Kingdom . |
| 2221139 | 1/1990 | United Kingdom . |

*Primary Examiner*—Tuan Nguyen
*Attorney, Agent, or Firm*—Ladas & Parry

[57] ABSTRACT

A unit for sampling and quality controlling tobacco items, in particular cigarettes, wherein a sample item, fed by a first conveyor along a first given path, is transferred automatically by a selectively operated spoon-shaped diverter along a second path to a second conveyor tangent to the first path. The sample item is fed to a support in which it is supported in facing relation to an optical control device. The sample item is inspected in the support and the optical control device emits signals as a function of the surface characteristics of the sample item.

9 Claims, 2 Drawing Sheets

UNIT FOR SAMPLING AND QUALITY CONTROLLING TOBACCO ITEMS, PARTICULARLY CIGARETTES

BACKGROUND OF THE INVENTION

The present invention relates to a unit for sampling and quality controlling tobacco items, particularly cigarettes.

The present invention may be used to advantage on cigarette manufacturing machines—to which the following description refers purely by way of example—for quality controlling individual sample cigarettes taken from the machines at predetermined intervals within the production cycle.

At present, sample cigarettes taken from specific parts of the machine are quality controlled by a skilled operator who, at regular intervals within the production cycle, takes a single sample and feeds it manually to a control station where, either manually or by means of instruments, the sample is quality controlled, for example, as regards length, the intensity and distance of the print from the filter, and/or correct alignment of the filter connecting strip.

Depending on whether any defects are detected on the sample, the operator then provides for manually adjusting the operating parameters of the machine.

By virtue of employing skilled labour both for controlling the surface characteristics of the sample and adjusting the machine, the above method is not only expensive but also unreliable.

SUMMARY OF THE INVENTION

It is an object of the present invention to provide a unit for quality controlling tobacco items, in particular cigarettes, designed to overcome the aforementioned drawbacks.

According to the present invention, there is provided a unit for sampling and quality controlling tobacco items, in particular cigarettes; the unit comprising first conveyor means for feeding the items along a first given path; diverting means located at a withdrawal station along said first path, and which provide for diverting at least one sample item from said first path and along a second path; and a control station for controlling the sample item, the control station comprising optical control means for emitting signals as a function of the characteristics of the sample item; characterized in that said control station comprises supporting means located adjacent to the optical control means and for supporting said sample item; second conveyor means being so positioned as to interfere with said second path, so as to receive each said sample item and transfer it to said supporting means.

BRIEF DESCRIPTION OF THE DRAWINGS

A number of non-limiting embodiments of the present invention will be described by way of example with reference to the accompanying drawings, in which.

DETAILED DESCRIPTION OF THE INVENTION

Figure 1:
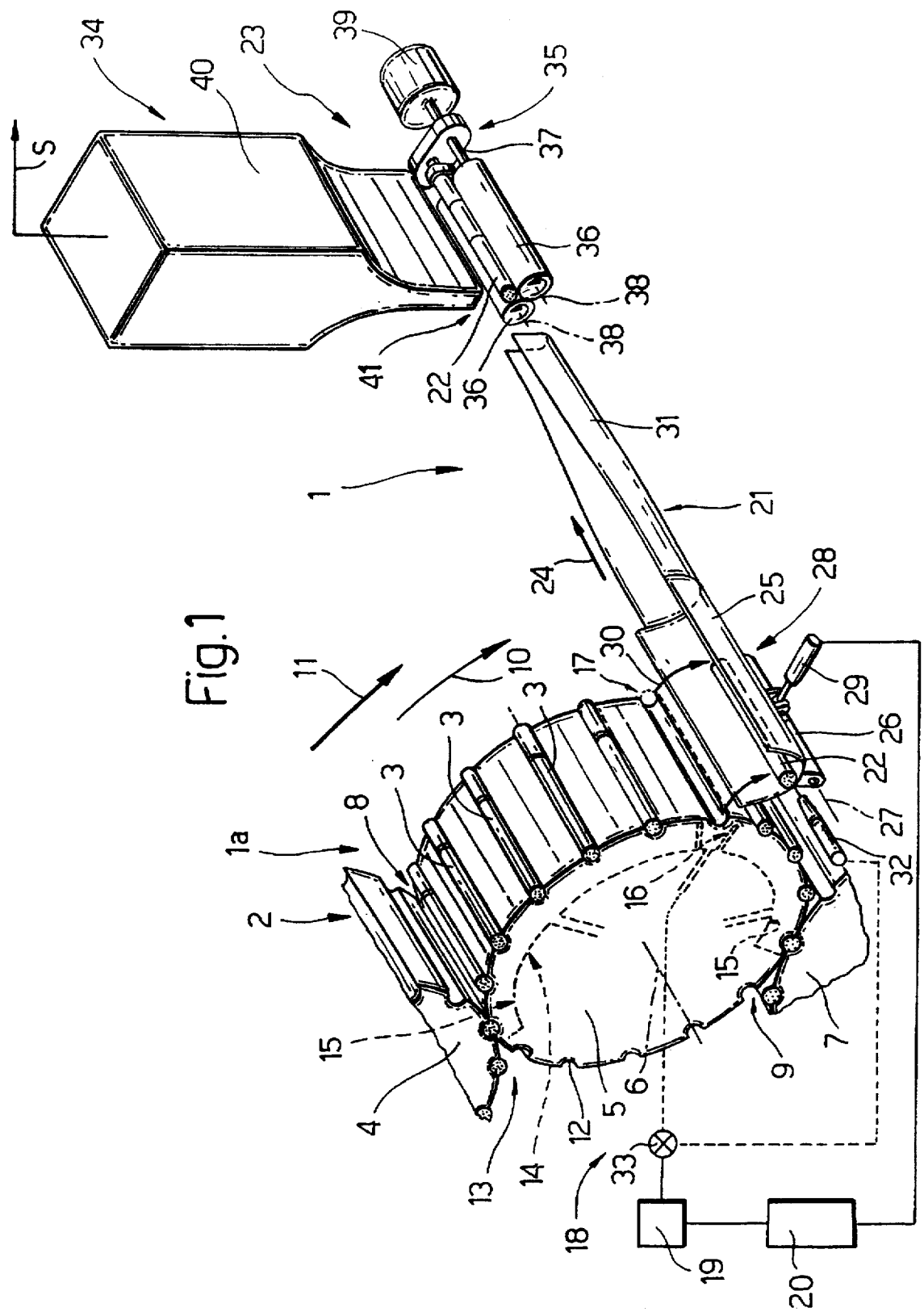
FIG. 1 shows a view in perspective of a first preferred embodiment of the unit according to the present invention.

Numeral 1 in FIG. 1 indicates a sampling and quality control unit forming part of a manufacturing machine 2 and comprising a conveyor 1a for a succession of cigarettes 3. Conveyor 1a comprises an input roller 4 rotating anticlockwise (in FIG. 1); an intermediate sampling roller 5 rotating clockwise (in FIG. 1) about its axis 6 and in time with roller 4; and an output roller 7 rotating anticlockwise (in FIG. 1) and in time with rollers 4 and 5. Roller 5 is tangent to rollers 4 and 7 at respective transfer stations 8 and 9, which define, along the periphery of roller 5, a sampling arc 10 forming part of the path 11 along which cigarettes 3 are fed through unit 1.

As they travel along arc 10, cigarettes 3 are housed inside respective seats 12 equally spaced about the periphery of roller 5 and communicating in known manner with a known suction system 13. System 13 comprises a fixed distributor 14, the suction chamber 15 of which extends over the whole of arc 10 with the exception of a small intermediate chamber 16 located along arc 10 at a withdrawal station 17, and forming part of a diverting device 18 which, when operated, provides for expelling cigarette 3 from the seat 12 communicating with chamber 16. In addition to chamber 16, diverting device 18 also comprises a pump 19 for feeding compressed air into chamber 16 under the control of a central control unit 20.

At withdrawal station 17, roller 5 cooperates with a conveyor device 21 for receiving sample cigarettes hereinafter indicated by 22—from roller 5 and feeding them to a control station 23.

Conveyor device 21 is substantially tangent to path 11 at station 17, is a pneumatic conveyor device extending in a direction 24 substantially parallel to axis 6, and comprises an input portion defined by a substantially U-section spoon 25 oriented parallel to direction 24 and presenting a bottom axial appendix 26 hinged to a fixed support (not shown) so as to rotate about an axis 27 parallel to direction 24. In addition to forming part of conveyor device 21, spoon 25 also forms part of a catch device 28 which also comprises an actuator 29 connected to appendix 26 and controlled by central unit 20 so as to rotate spoon 25 to and from an operating position wherein its concavity faces upwards and interferes with the path 30 along which sample cigarette 22 travels on leaving seat 12 at station 17.

In addition to spoon 25, conveyor device 21 also comprises a guide channel 31 parallel to axis 27 and aligned with spoon 25 when this is in the operating position at withdrawal station 17; and an ejector nozzle 32 aligned with channel 31, located upstream from spoon 25 in direction 24, and connected to pump 19 by a diverting device 33 controlled by central unit 20 so as to direct the delivery of pump 19 towards chamber 16 or towards nozzle 32.

Control station 23 is positioned facing the output end of channel 31, and comprises an optical control device 34 for emitting an output signal S as a function of the surface characteristics of sample cigarette 22; and a rotary supporting device 35 aligned with channel 31, and which provides for supporting sample cigarette 22 and for rotating it about its axis facing optical control device 34.

In the FIG. 1 example, device 35 comprises a pair of side by side rollers 36 supported on respective shafts 37 and rotated in the same direction about their respective axes 38, parallel to axis 27, by a device 39; and optical control device 34 comprises a linear camera 40 facing rollers 36 and presenting a linear optical detecting system 41 extending along rollers 36 and comprising in known manner an array of photosensors (not shown).

In actual use, at predetermined time intervals, central control unit 20 operates pump 19 to feed compressed air into chamber 16 and detach a sample cigarette 22 from respective seat 12 as the sample cigarette 22 travels through withdrawal station 17.

At the same time, control unit 20 moves spoon 25 from the idle position clear of station 17, to the FIG. 1 operating position wherein it interferes with the path 30 travelled by cigarette 22 expelled from seat 12, so as to catch cigarette 22 and position it in line with channel 31. At this point, control unit 20 operates diverting device 33 so as to feed compressed air to nozzle 32 which transfers cigarette 22 from spoon 25 to control station 23 along channel 31.

On leaving channel 31, cigarette 22 is deposited onto rollers 36 which are activated by device 39 to expose the entire surface of cigarette 22 to optical system 41 of camera 40, and to enable camera 40 to emit signal S which may be used for automatically adjusting the functional and/or structural parameters of machine 2.

Figure 2:
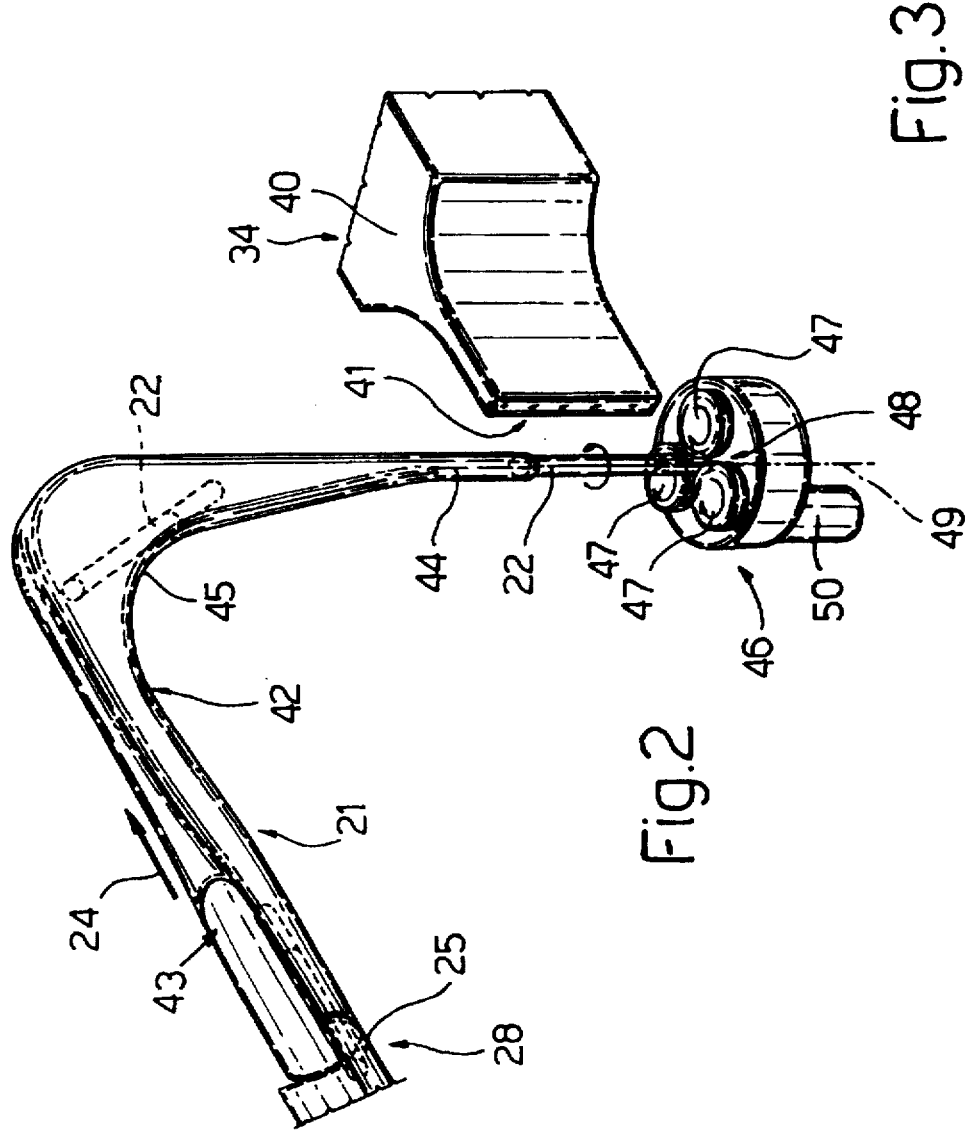
FIG. 2 shows a partial view in perspective of a second preferred embodiment of the unit according to the present invention.

In the FIG. 2 embodiment, channel 31 is replaced by a channel 42 which presents a straight input portion 43 parallel to axis 27, and a tubular output portion 44 perpendicular to portion 43 and connected to it by a curved tubular intermediate portion 45. More specifically, portion 44 is positioned vertically over a supporting device 46 which comprises three disks 47 defining a cavity 48 with an axis 49 coaxial with tubular portion 44. Disks 47 are connected to a drive device 50 by which they are all rotated in the same direction to rotate a cigarette 22 positioned with one end engaged inside cavity 48. Cigarette 22 is thus rotated about axis 49 and in front of camera 40 which, in this case, is positioned with optical system 41 upright and parallel to axis 49.

Figure 3:
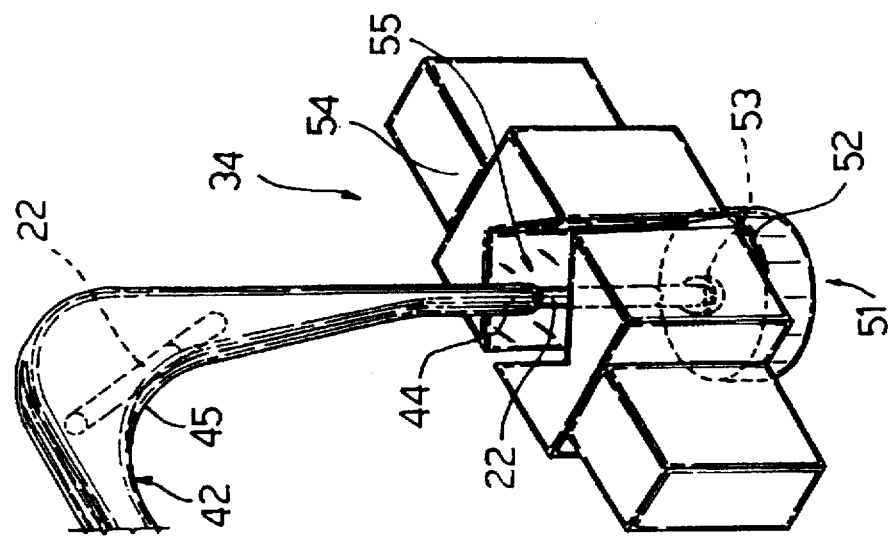
FIG. 3 shows a partial view in perspective of a third preferred embodiment of the unit according to the present invention.

In the FIG. 3 embodiment, supporting device 46 is replaced by a supporting device 51 which comprises a fixed plate 52 located beneath the free end of tubular portion 44, and presenting a vertical sleeve 53 defining a seat coaxial with tubular portion 44 and for receiving the end of cigarette 22. As supporting device 51 in the FIG. 3 embodiment is fixed, camera 40 is replaced by a camera 54 comprising two matrix optical systems 55 located between output portion 44 of conveyor device 21 and sleeve 53, and defined in known manner (not shown) by respective numbers of photosensors arranged on the surfaces of two dihedrons surrounding cigarette 22 engaged in the seat defined by sleeve 53.

I claim:

1. A unit for sampling and quality controlling tobacco items; the unit comprising first conveyor means for feeding the items along a first given path; diverting means located at a withdrawal station along said first path, and which provides for diverting at least one sample item from said first path and along a second path; and a control station for controlling the sample item, the control station comprising optical control means for emitting signals as a function of the characteristics of the sample item; said control station comprising supporting means located adjacent to the optical control means for supporting said sample item; second conveyor means positioned to interfere with said second path, so as to receive each said sample item and transfer it to said supporting means; said second conveyor means comprising an input portion including a spoon located at the withdrawal station for receiving said sample item; and an output portion aligned with said supporting means, said input portion further comprising actuating means for moving said spoon to and from said position of interference.

2. A unit as claimed in claim 1, wherein the second conveyor means comprises a pneumatic conveyor having a channel for guiding said sample item.

3. A unit as claimed in claim 1, wherein the supporting means is a rotary support means.

4. A unit as claimed in claim 3, wherein the rotary supporting means comprises a pair of side by side rollers having respective substantially horizontal axes parallel to each other; and a drive device for rotating said two rollers in the same direction about their respective aces.

5. A unit as claimed in claim 4, wherein said optical control means comprises a linear camera facing said rollers and including an optical detecting system extending along the rollers.

6. A unit as claimed in claim 3, wherein the rotary supporting means comprises at least three side by side disks defining a cavity aligned with said output portion for receiving an end portion of a sample item; and a drive device for rotating said disks in the same direction about their respective axes.

7. A unit as claimed in claim 6, wherein said optical control means comprises a linear camera including an optical detecting system extending parallel to the axes of said disks.

8. A unit as claimed in claim 1, wherein the supporting means is a fixed supporting means.

9. A unit as claimed in claim 8, wherein the optical control means comprises a matrix camera located between the output portion of the second conveyor means and said fixed supporting means.

* * * * *